(12) United States Patent
Chen et al.

(10) Patent No.: US 11,999,962 B2
(45) Date of Patent: Jun. 4, 2024

(54) METHOD OF INCREASING THE EFFECTIVE TILLER NUMBER OF RICE PLANT

(71) Applicant: Zhejiang Normal University, Zhejiang (CN)

(72) Inventors: Xifeng Chen, Zhejiang (CN); Bojun Ma, Zhejiang (CN); Dan Zhou, Zhejiang (CN); Junjie Yuan, Zhejiang (CN)

(73) Assignee: Zhejiang Normal University, Jinhua (CN)

( * ) Notice: Subject to any disclaimer, the term of this patent is extended or adjusted under 35 U.S.C. 154(b) by 275 days.

(21) Appl. No.: 17/521,857

(22) Filed: Nov. 9, 2021

(65) Prior Publication Data

US 2022/0056467 A1   Feb. 24, 2022

Related U.S. Application Data

(63) Continuation of application No. PCT/CN2020/094615, filed on Jun. 5, 2020.

(30) Foreign Application Priority Data

May 10, 2019 (CN) .......................... 201910387819.0

(51) Int. Cl.
*C12N 15/82* (2006.01)

(52) U.S. Cl.
CPC ..... *C12N 15/8262* (2013.01); *C12N 15/8261* (2013.01)

(58) Field of Classification Search
None
See application file for complete search history.

(56) References Cited

FOREIGN PATENT DOCUMENTS

| CN | 110106199 A | * | 8/2019 | ......... C12N 15/8261 |
| CN | 107904246 B |   | 10/2020 | |

OTHER PUBLICATIONS

Kumar et al (RNA-seq analysis reveals the genes/pathways responsible for genetic plasticity of rice to varying environmental conditions on direct-sowing and transplanting. Scientific Report. 1-22, 2022) (Year: 2022).*
Kim et al (CF297019, published Aug. 14, 2003) (Year: 2003).*
Rounsley et al (De Novo Next Generation Sequencing of Plant Genomes. Rice 2:35-43, 2009) (Year: 2009).*
Bossa-Castro (Exploiting Rice Diversity to Uncover Durable and Broad-Spectrum Resistance. Ph.D. Dissertation. Spring 2018) (Year: 2018).*

* cited by examiner

*Primary Examiner* — Charles Logsdon
*Assistant Examiner* — Wayne Zhong

(57) ABSTRACT

Provided is a method of increasing the effective tiller number of a rice plant, including overexpressing a gene having a nucleic acid sequence as shown in SEQ ID NO: 1 in the rice plant. The gene encodes a protein which interacts with MOC1 in the rice plant.

1 Claim, 1 Drawing Sheet
Specification includes a Sequence Listing.

SEQUENCE LISTING

```
<160> NUMBER OF SEQ ID NOS: 9

<210> SEQ ID NO 1
<211> LENGTH: 309
<212> TYPE: DNA
<213> ORGANISM: Oryza sativa

<400> SEQUENCE: 1
atgggagact catcatcctc agcttcgtac atcagaatgg ttcaccacct gatagagaag      60
tgcatttgct tcaacctgaa caaggaggag tgcatggagg ccctggagaa gcatgccaac     120
atcaaccctg tcgtcacttc cacagtatgg aaggagctga agaaggagaa caaggagttc     180
ttcgagacct acaacaagga cagggcggag cgcaacatcg aggcggagac gatgcagcgg     240
atccagaaga tgctctccga cgccgcggca tccaagggct ccgacgacga cgacgacgac     300
gagagctag                                                             309

<210> SEQ ID NO 2
<211> LENGTH: 31
<212> TYPE: DNA
<213> ORGANISM: Artificial sequence
<220> FEATURE:
<223> OTHER INFORMATION: primer F1

<400> SEQUENCE: 2
cggggtacca gatagataag taagcagtga g                                     31

<210> SEQ ID NO 3
<211> LENGTH: 30
<212> TYPE: DNA
<213> ORGANISM: Artificial sequence
<220> FEATURE:
<223> OTHER INFORMATION: primer R1

<400> SEQUENCE: 3
aaaactgcag gatgcatgct tacggcacat                                       30

<210> SEQ ID NO 4
<211> LENGTH: 20
<212> TYPE: DNA
<213> ORGANISM: Artificial sequence
<220> FEATURE:
<223> OTHER INFORMATION: primer P1

<400> SEQUENCE: 4
ccaggcttta cactttatgc                                                  20

<210> SEQ ID NO 5
<211> LENGTH: 20
<212> TYPE: DNA
<213> ORGANISM: Artificial sequence
<220> FEATURE:
<223> OTHER INFORMATION: primer P2

<400> SEQUENCE: 5
gcgattaagt tgggtaacgc                                                  20

<210> SEQ ID NO 6
<211> LENGTH: 22
```

```
<212> TYPE: DNA
<213> ORGANISM: Artificial sequence
<220> FEATURE:
<223> OTHER INFORMATION: primer F2

<400> SEQUENCE: 6
ggagcttgct gatccagtag tc                                          22

<210> SEQ ID NO 7
<211> LENGTH: 22
<212> TYPE: DNA
<213> ORGANISM: Artificial sequence
<220> FEATURE:
<223> OTHER INFORMATION: primer R2

<400> SEQUENCE: 7
tagctagagc tcatgtgaag ag                                          22

<210> SEQ ID NO 8
<211> LENGTH: 21
<212> TYPE: DNA
<213> ORGANISM: Artificial sequence
<220> FEATURE:
<223> OTHER INFORMATION: primer F3

<400> SEQUENCE: 8
tggcatctct cagcacattc c                                           21

<210> SEQ ID NO 9
<211> LENGTH: 20
<212> TYPE: DNA
<213> ORGANISM: Artificial sequence
<220> FEATURE:
<223> OTHER INFORMATION: primer R3

<400> SEQUENCE: 9
tgcacaatgg atgggtcaga                                             20
```

METHOD OF INCREASING THE EFFECTIVE TILLER NUMBER OF RICE PLANT

CROSS-REFERENCE TO RELATED APPLICATION

The present application is a continuation application of PCT Application No. PCT/CN2020/094615 filed on Jun. 5, 2020, which claims the benefit of Chinese Patent Application No. 201910387819.0 filed on May 10, 2019, the disclosure of which is hereby incorporated by reference in their entirety.

REFERENCE TO SEQUENCE LISTING

The Sequence Listing is submitted as an ASCII formatted text file via EFS-Web, with a file name of "Sequence_listing.TXT", a creation date of Nov. 8, 2021, and a size of 2,275 bytes. The Sequence Listing filed via EFS-Web is part of the specification and is incorporated in its entirety by reference herein.

TECHNICAL FIELD

This invention relates to method of increasing the effective tiller number of rice plant, and belongs to the field of molecular genetics in plant.

BACKGROUND ART

The number of effective panicles per unit area, the grains number per panicle and 1000-grain weight mainly determine the rice yield. The number of effective panicles is directly related to the tillers number of rice plant. Tillers are the branches of gramineous plants, such as rice, that occur below the ground or close to the ground. The tillers which will head and bear grains are called effective tillers, or are called ineffective tillers. The number of effective tillers directly determines the number of effective panicles in rice.

So far, researches indicated that rice tillering were regulated by the multiple genes, among which the transcription factor MOC1 and its interaction protein TAD1 are the mainly regulating factors for rice tillering, mediating the initiation, growth and development of the tillers' buds. The mutant of rice mod has only a single tiller, while the mutant tad1 significantly increases the tillers number. TAD1 interacts with MOC1 to degrade MOC1 through the ubiquitination of 26S-proteasome pathway, and functions on the upstream of MOC1 to regulate tillering in rice.

The Invention "Application of gene for improving photosynthesis efficiency of rice" (Patent NO. ZL201711469003.X) informed that the gene LOC_Os05g38680 can increase the photosynthesis in rice, specifically to increase the content of chlorophyll a and chlorophyll b in rice leaves.

DISCLOSURE OF THE INVENTION

The technical problem to be solved by the invention is to provide the application of a gene in increasing the number of effective tillers in rice.

To solve this problem, the present invention provides an application of gene in increasing the number of effective tillers in rice. The nucleotide sequence of this gene is shown as SEQ ID NO: 1. In particular, the present invention provide a method of increasing the effective tiller number of a rice plant, comprising overexpressing a gene having a nucleic acid sequence as shown in SEQ ID NO: 1 in the rice plant.

Over expression of this gene significantly increased the number of effective tillers in the transgenic rice plants.

The technical scheme of the invention is as follows:

Gene LOC_Os05g38680 (SEQ ID NO: 1) sequence was amplified from the total cDNA of rice by PCR and constructed into an over-expressional vector, which was genetically transformed into a wild-type rice variety Nipponbare by *Agrobacterium*-mediated method. Two positive transgenic lines named OE1 and OE2 were identified. As the result of the teal-time PCR, the expressional levels of gene LOC_Os05g38680 in the two transgenic lines, OE1 and OE2, were significantly higher than that in the wild-type control Nipponbare (FIG. 1). At rice mature stage, the effective tiller number of the tow transgenic lines were significantly more than that of the wild-type control Nipponbare (FIG. 2 and FIG. 3), indicating that overexpression of LOC_Os05g38680 gene can effectively increase the number of effective tillers in rice.

Previously, the invention 'Application of gene for improving photosynthesis efficiency of rice' (Patent NO. ZL201711469003.X) has informed that gene LOC_Os05g38680 could be used to improve the photosynthesis of rice. According to the common sense in the field, the advantageous performance from improving the photosynthesis of rice is generally to increase the net-photosynthetic rate and the grain biomass of rice, and is not inevitably related to increase the number of effective tillers of rice.

It has shown that genes PGL11 and CO11b involved in the process of photosynthesis have no significant effect on the tiller number of rice. Similarly, genes involved in regulation of tiller development, such as MOC1, MOC2, TAD1, LAX1, LAX2, D53, and D14, also have no significant effect on the photosynthetic efficiency of rice. Therefore, the published invention 'Application of gene for improving photosynthesis efficiency of rice' cannot provide the technical enlightenment for this invention.

In summary, this invention provided an application of gene LOC_OS05G38680 in rice breeding. Overexpression of LOC_OS05G38680 gene can significantly increase the effective-tiller number of the transgenic rice plants, which has potential application value in high-yield breeding.

BRIEF DESCRIPTION OF THE DRAWINGS

The specific embodiments of this invention are described in detail with the accompanying drawings.

Figure 1:
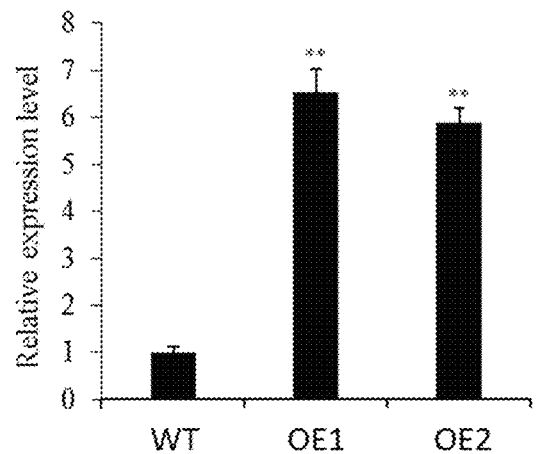
FIG. 1 shows the expression level of gene LOC_OS05G38680 in the rice transgenic lines.

For all figures, WT refers to the wild-type control variety Nipponbare; OE1 and OE2 refer to the two different rice transgenic lines overexpressing gene LOC_OS05G38680. '*' and '**' indicate the significance (P<0.05) and the extreme significance (P<0.01) by t-test between the transgenic line and the wild-type control.

DETAILED DESCRIPTION OF THE EMBODIMENTS

Step 1. Extraction of Total RNA from Rice and Synthesis of cDNA

Rice total RNA was extracted from the leaves of the wild-type variety Nipponbare by RNeasy Plant Mini Kit (QIAGEN, Germany) according to the product's instructions, and was reversely transcribed into the cDNA by PrimeScript™ 1st Strand cDNA Synthesis Kit (TaKaRa, Japan) according to the product's instructions.

Step 2. PCR Amplification of Gene LOC_Os05g38680

PCR amplification of gene LOC_Os05g38680 was carried by PrimeSTAR® HS DNA Polymerase (TaKaRa, Japan). The sequences of the primers are F1: 5'-CGGGGTACCAGATAGATAAGTAAGCAGTGAG-3' (SEQ ID NO: 2) and R1: 5'-AAAACTGCAGGATG-CATGCTTACGGCACAT-3' (SEQ ID NO: 3). The reaction solution of PCR was prepared according to the product's instructions, and PCR process were used as: 5 min at 95° C.; 10 sec at 98° C. for denaturation, 15 sec at 55° C. for annealing, 30 sec at 72° C. for extension, 30 cycles; and 5 min at 72° C.

Step 3. Enzymes Digestion and Purification of the PCR Products

The PCR products of gene LOC_Os05g38680 were purified bye the AxyPrep PCR cleaning kit (Axygen, USA) according to the product's instructions. Then, the purified products were digested by two restriction enzymes, Kpn I and Pst I (TaKaRa, Japan), and the digestion system included 1 μL Kpn I, 1 μL Pst I, 3 μl Buffer M (TaKaRa company restriction enzyme Buffer M), 10 μL PCR product, ddH$_2$O to make up to 20 μL, and then was incubated at 37° C. for 4 h. Finally, the digestion products were purified by the AxyPrep PCR cleaning kit (Axygen, USA) again.

Step 4. Enzymes digestion and purification of pCAM-BIA1300-2×35S vector

The plasmid of vector pCAMBIA1300-2×35S was digested and purified according to the method in Step 3.

Step 5. Overexpression Vector Construction of Gene LOC_Os05g38680

① The purified products obtained in Step 3 and Step 4 were ligated by the T4 ligase Kit (Promega, USA). The ligation system included 1 μL digested plasmid of the pCAMBIA1300-2×35S vector, 2 μL digested PCR fragment of gene LOC_Os05g38680, 0.5 μL T4 ligase, 1 μL ligation Buffer, ddH$_2$O supplement to 10 μL, and then was incubated overnight (12 h) at 4° C.

② Ten μL ligation products obtained from step ① were mixed with the bacterial competent cells of JM109 and incubated for 30 min in ice bath; then the bacterial mixture was incubated in water bath at 42° C. for 90 s and immediately transferred on ice for 10 min; 800 μL LB medium without any antibiotics was added into the bacterial mixture and incubated at 37° C. for 1 h on the shaker; finally, the bacterial mixture was spread on the LB medium plate containing Kanamycin (25 mg/L) and incubated at 37° C. overnight.

③ Monoclonal colonies on the plate were separately picked into test tubes with 4 mL of LB medium (Kanamycin 25 mg/L), and incubated overnight at 37° C. with a rotational speed 200 r/min on the shaker. the bacterial fluid of each tubes was identified by PCR using the 2×Taq PCR premix reagent (Tiangen, Beijing). PCR reaction system included 1 μL bacteria fluid, 10 μL 2×Taq PCR MasterMix II, 1 μL F1+R1 primers (10 μM), ddH$_2$O up to 20 μL. The PCR process were used as: 5 min at 94° C.; 30 sec at 94° C. for denaturation, 30 sec at 55° C. for annealing, 30 sec at 72° C. for extension, 35 cycles; and 5 min at 72° C. Then, 5 μL PCR products of each reaction was detected by agarose-gel electrophoresis.

④ The positive colonies identified by PCR were sent to the biotechnology company for sequencing the sequence of gene LOC_OS05G38680 inserted into the vector pCAM-BIA-1300. The universal primers P1: 5'-CCAGGCTTTA-CACTTTATGC-3' (SEQ ID NO: 4) and P2: 5'-GCGAT-TAAGTTGGGTAACGC-3' (SEQ ID NO: 5) were used for sequencing. The vector containing a correct sequence of gene LOC_OS05G38680 was used for further rice transformation. The nucleotide sequence of gene LOC_Os05g38680 in the vector was shown in SEQ ID NO: 1.

Step 6. Genetic Transformation of Rice

The vector constructed from Step 5 was transformed into a wild-type rice variety Nipponbare using the method of Nishimura et al. (Nishimura et al, Nat Protoc, 2006) to obtain the transgenic rice plants.

Step 7. Identification of the Transgenic Plants

The extraction of the total RNAs from the transgenic plants and cDNA synthesis were followed by the methods described in Step 1. The expression levels of gene LOC_Os05g38680 in the transgenic plants were analyzed by Real-time PCR using the primer pair F2: 5'-GGAGCTTGCTGATCCAGTAGTC-3' (SEQ ID NO: 6) and R2: 5'-TAGCTAGAGCTCATGTGAAGAG-3' (SEQ ID NO: 7). The SYBR® Premix Ex Taq™ II Kit (TakaRa, Japan) was used for Real-time PCR, and the reaction system included 10 μL SYBR® Premix Ex Taq® II, 2 μL cDNA template, 1 μL F2+R2 primers (10 μM each), 0.4 μL ROX Reference Dye, ddH$_2$O up to 20 μL. Rice housekeeping gene Actin was used for the standard normalization, the PCR primers are F3: 5'-TGGCATCTCTCAGCACATTCC-3' (SEQ ID NO: 8) and R3: 5'-TGCACAATG-GATGGGTCAGA-3' (SEQ ID NO: 9). PCR process was performed as: 95° C. for 30 s; 95° C. for 5 s and 60° C. for 30 s, 40 cycles. Three replicates were done for each sample, and the data were analyzed using the $2^{-\Delta\Delta C_T}$ method (Livak K J and Schmittgen T D, Methods, 2001), and the significances between the transgenic plants and the wild-type control were analyzed by the t-test method.

As the results of Real-time PCR, the two transgenic lines (OE1 and OE2) were identified with high expression levels of gene LOC_Os05g38680, which were significantly higher than that in the wild-type control (FIG. 1)

Step 8. Statistical Investigation of Effective Tillers Number in the Transgenic Lines In May, rice seeds were sowed in south China, and transplanted in fields at June in the same year. After maturity (October in the same year), each 20 plants were randomly selected from the two transgenic lines (OE1 and OE2) and the wild-type control Nipponbare for investigating the number of effective tillers per plant. The significances between the two transgenic lines and the wild-type control were analyzed by the t-test.

Figure 2:
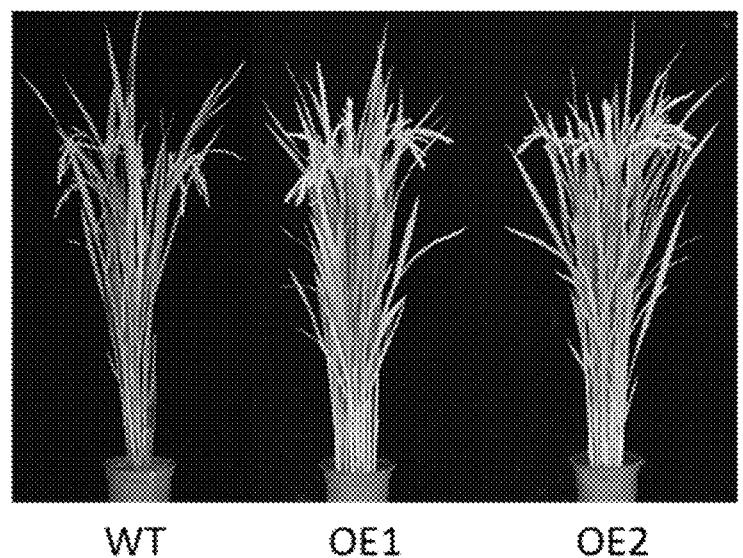
FIG. 2 shows plant phenotypes of the rice transgenic lines overexpressing gene LOC_OS05G38680.
Figure 3:
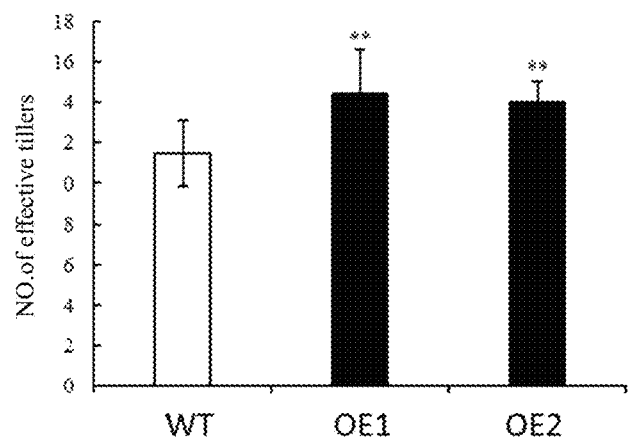
FIG. 3 shows statistics of the effective tiller number of the rice transgenic lines overexpressing gene LOC_OS05G38680.

As a result of the statistical investigation, the number of effective tillers per plant both in the two transgenic lines (OE1 and OE2) were significantly higher than that in the wild-type control (FIG. 2 and FIG. 3), indicating that enhancing the expression level of gene LOC_Os05g38680 could effectively increase the number of effective tillers in rice.

Finally, it is important to note that the above lists are only specific embodiments of the present invention. Obviously, the invention is not limited to the above embodiments, but can also have a lot of deformation. All the deformation that the general technical personnel in this field can directly derive or associate with the contents disclosed in this field should be considered as the scope of protection of the invention.

The invention claimed is:

1. A method of increasing the effective tiller number of a rice plant, comprising overexpressing a gene having a nucleic acid sequence of SEQ ID NO: 1 in the rice plant, wherein a heterologous promoter driving overexpression of SEQ ID NO: 1 causes the overexpression.

* * * * *